United States Patent [19]

Calomino

[11] Patent Number: 4,986,132
[45] Date of Patent: Jan. 22, 1991

[54] FULLY ARTICULATED FOUR-POINT-BEND LOADING FIXTURE

[75] Inventor: Anthony M. Calomino, Cleveland, Ohio

[73] Assignee: The United States of America as represented by the Administrator of the National Aeronautics and Space Administration, Washington, D.C.

[21] Appl. No.: 458,274

[22] Filed: Dec. 28, 1989

[51] Int. Cl.⁵ .............................................. G01N 3/20
[52] U.S. Cl. ........................................................ 73/852
[58] Field of Search ............................ 73/812, 849–854

[56] References Cited

U.S. PATENT DOCUMENTS

| 2,243,842 | 6/1941 | Fearn | 265/1.6 |
| 2,732,712 | 1/1956 | Reed | 73/812 |
| 3,170,321 | 2/1965 | Sullivan et al. | 73/100 |
| 3,332,281 | 7/1967 | Spangler | 73/100 |
| 3,937,072 | 2/1976 | Huydts et al. | 73/100 |
| 4,677,856 | 7/1987 | Fischer | 73/850 |
| 4,730,498 | 3/1988 | Blanch | 73/852 |

FOREIGN PATENT DOCUMENTS

| 0069140 | 3/1987 | Japan | 73/849 |
| 1100531 | 6/1984 | U.S.S.R. | 73/849 |

OTHER PUBLICATIONS

Tsvikenvich et al., "Device for Static Bending Testing of Samples at Different Temperature and Media", Ind. Lab (U.S.A.), vol. 43, No. 3 (Mar. 1977).

Primary Examiner—Robert Raevis
Attorney, Agent, or Firm—Gene E. Shook; John R. Manning; James A. Mackin

[57] ABSTRACT

A fully articulated four-point-bend loading fixture for MOR and fracture toughness specimens utilizes an upper loading plate in combination with a lower loading plate. The lower plate has a pair of spring loaded ball bearings which seat in V-shaped grooves located in the upper plate. The ball bearings are carried in the arms of the lower plate. A load is applied to the specimen through steel rollers, one large roller and one smaller roller each located on both the upper and lower plates. The large rollers have needle roller bearings which enable a single loading roller to rotate relative to the plate to which it is attached.

11 Claims, 3 Drawing Sheets

FULLY ARTICULATED FOUR-POINT-BEND LOADING FIXTURE

ORIGIN OF THE INVENTION

The invention described herein was made by an employee of the United States Government and may be manufactured and used by or for the Government for governmental purposes without the payment of any royalties thereon or therefore.

TECHNICAL FIELD

This invention is concerned with an improved fixture for modulus of rupture (MOR) and fracture toughness specimens. The invention is particularly directed to a fully articulated four-point-bend loading fixture.

Specimens used for modulus of rupture (MOR) and chevron-notched four-point bend tests are made of brittle materials. The size specifications for those specimens are established by the Army Materials and Mechanics Research Center (AMMRC) now known as the U.S. Army Materials Technology Laboratory.

One prior art fixture has been specifically designed by AMMRC to perform brittle-material strength tests. However, the prior art fixture does not articulate and cannot be used on specimens which are warped, twisted or non-parallel. Reference is made to Ad-A160 873, "Commentary on U.S. Army Standard Test Method for Flexural Strength of High Performance Ceramics at Ambient Temperature."

An improved prior art fixture is designed to accept beams with twist, warp, or non-parallelism. However, the design of this fixture is considerably more complex than the previously mentioned prior art fixture. See "Reduction of Errors in Ceramic Bend Test", *Journal of American Ceramic Society*, 59, 5-6, 1976.

A major problem encountered in the AMMRC fixture is that the device does not accommodate less than perfect beams. Although the improved fixture accommodates imperfect test specimens, the structure is quite complicated.

It is, therefore, an object of the present invention to provide loading for modulus of rupture and chevron-notched four-point bend specimens made of brittle materials.

Another object of the invention is to provide a loading fixture which will accommodate specimens having size specifications established by the U.S. Army Materials Technology Laboratory.

PRIOR ART

U.S. Pat. No. 2,243,842 to Fearn discloses a device for indicating springiness of strands which includes idler rollers that support the ends of the strand. A wheel applies a force to the strand.

U.S. Pat. No. 3,170,321 to Sullivan et al is concerned with a fatigue testing machine. The device utilizes a gripping member on the ends of the specimen and rollers mounted in ball bearing races.

U.S. Pat. No. 3,332,281 to Spangler is directed to a device for measuring biaxial stress-strain. The apparatus includes a specimen support member having O-rings to support the ends of the specimen.

U.S. Pat. No. 3,937,072 to Huydts et al is concerned with a system for measuring deformation in a bending press. The press has rollers mounted on a pivotable yoke. This yoke is utilized in combination with a central roller.

U.S. Pat. No. 4,730,498 to Blanch describes a fixture for holding a bending test specimen. This structure includes a gripping member mounted on a carriage through canted rollers.

DISCLOSURE OF THE INVENTION

This invention is directed to a fully articulated four-point-bend loading fixture for a modulus of rupture and fracture toughness specimen. The fixture includes an upper loading plate in combination with a lower loading plate. The lower plate includes a pair of spring loaded ball bearings which seat in V-shaped grooves located in the upper plate. The ball bearings are in the arms of the lower plate.

Load is applied to the specimen through steel rollers, one large roller and one smaller roller, each located on both the upper and lower plates. The large rollers have associated therewith needle roller bearings to enable a single loading roller to rotate on an axis at right angles to the axis of the roller.

BRIEF DESCRIPTION OF THE DRAWING

The advantages and novel features of the invention will be more fully apparent from the following detailed description when read in connection with the accompanying drawings wherein.

BEST MODE FOR CARRYING OUT THE INVENTION

Figure 1:
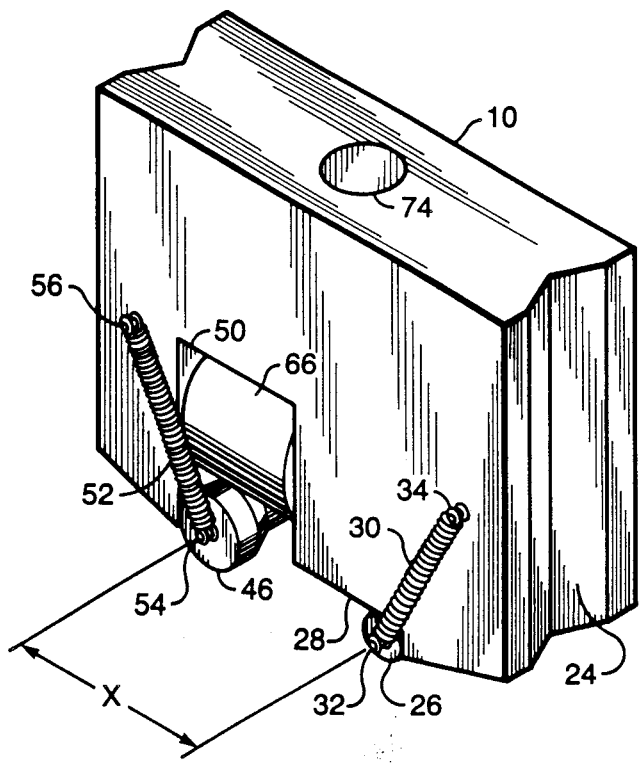
FIG. 1 is a perspective view of an upper loading plate constructed in accordance with the present invention to provide a predetermined fixed loading span.

Referring now to the drawing, there is shown a self-aligning, fully articulated system for loading brittle material beam specimens in a four-point, or pure bending configuration. A fixed span X is provided by an upper loading plate 10 shown in FIG. 1. Such a fixed span of 20 millimeters meets the aforementioned requirements.

Figure 2:
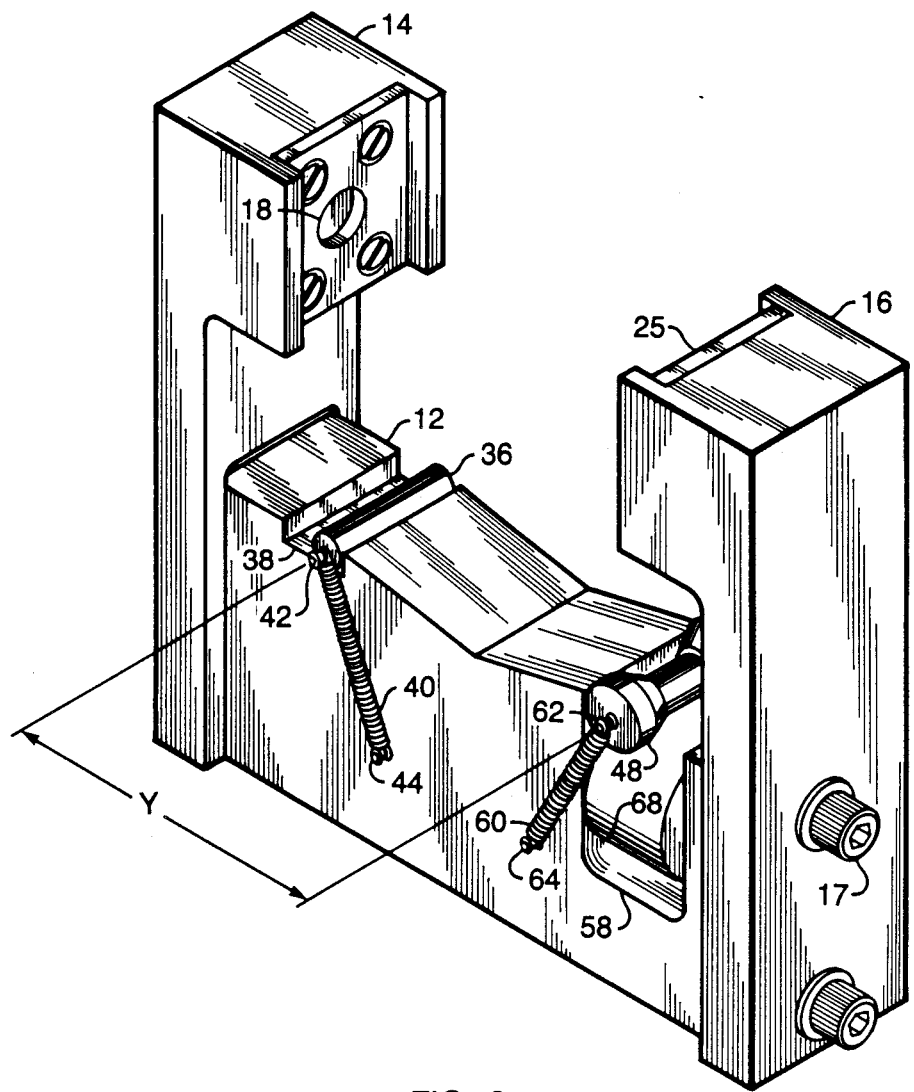
FIG. 2 is a perspective view of a lower loading plate constructed in accordance with the present invention to provide a predetermined outer span.

This upper loading plate 10 is automatically centered about a 40 millimeter outer span Y on a lower loading plate 12 shown in FIG. 2. A pair of upwardly extending alignment arms 14 and 16 are secured to opposite ends of the lower loading plate 12 by location bolts 17 as shown in FIGS. 2 and 3.

Figure 3:
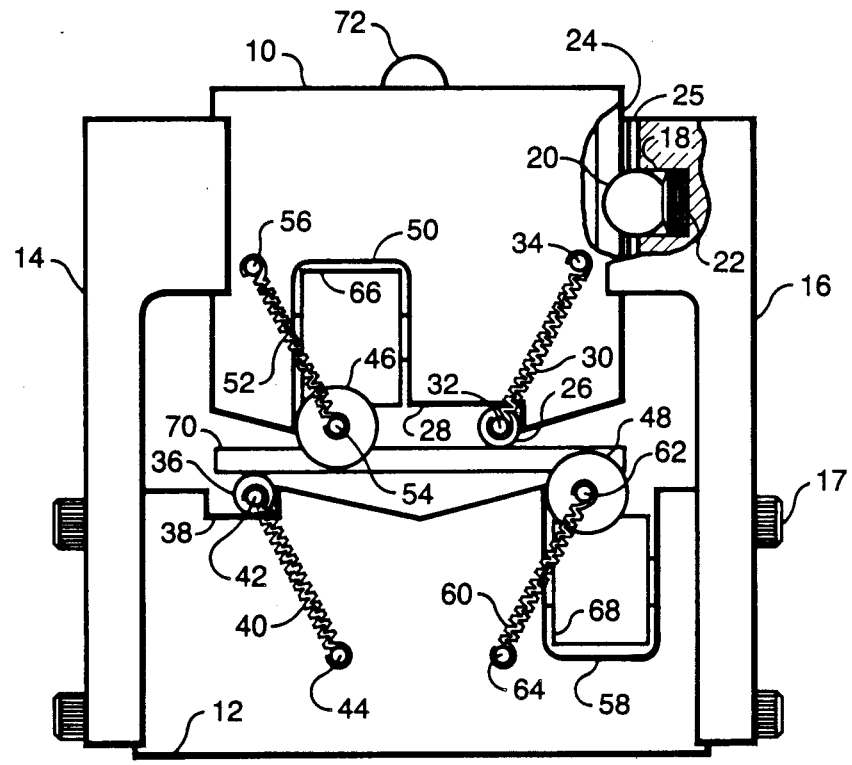
FIG. 3 is a front elevation view with portions broken away showing the assembly of the fixture which comprises the upper loading plate operably mounted over the lower loading plate.

Each of these arms has a hole 18 which encloses a ball bearing 20 shown in FIG. 3. A spring 22 in the bottom of the hole 18 urges the respective ball 20 into engagement with a mating V-shaped groove 24 in the upper plate 10. This fitting of the ball bearings 20 carried by the alignment arms into the two V-shaped grooves 24 on either side of the upper loading plate 10 accommodates rotation of this upper loading plate with respect to the lower loading plate 12. Portions of the ends of the upper plate on opposite sides of the V-grooves engage suiteable bearing plates 25 mounted on the arm 14 and 16.

A hardened steel roller 26 is mounted for movement in a recess 28 in the upper loading plate 10. Referring to FIG. 3, the roller 26 is positioned by a pair of springs 30, one on each side of the upper loading plate 10. One end of each spring 30 is secured to each end of an axle 32 which extends through the roller 26. The opposite end of each spring is mounted on a pin 34 on either side of the upper loading plate 10.

A similar hardened steel roller 36 is mounted for rolling motion in a recess 38 in the lower loading plate 12 as shown in FIGS. 2 and 3. A pair of springs 40, one on each side of the lower loading plate 12, positions the roller 36 in the recess 38 as shown in FIG. 3. One end of each spring 40 is secured to an end of an axle 42 which extends through the roller 36. The opposite end of each spring 40 is mounted on a pin 44 which extends from the lower loading plate 12. It will be appreciated that pins 44 are provided in both faces of the lower loading plate 12.

An important feature of the invention is the provision of large diameter hardened steel rollers 46 and 48. Referring now to FIGS. 1 and 3, the roller 46 is mounted for movement in a slot 50 in the upper loading plate 10. The roller 46 is positioned by a pair of springs 52, one on each side of the upper loading plate 10, as shown in FIG. 3. One end of each spring 52 is secured to each end of an axle 54 which extends through the roller 46. The opposite end of each spring is mounted on a pin 56 on either side of the upper loading plate 10.

Referring to FIGS. 2 and 3, the other large diameter hardened steel roller 48 is similarly mounted in a slot 58 in the lower loading plate 12 by a pair of springs 60, one on each side of the lower loading plate 12. One end of each spring 60 is secured to an end of an axle 62 which extends through the roller 48. The opposite end of each spring 60 is mounted on a pin 64 on either side of the lower loading plate 12.

A unique innovation found in this loading fixture is that the large diameter rollers rest on needle roller bearings. More particularly, the roller 46 is urged into engagement with a needle roller bearing 66 which extends through the slot 50. In a similar fashion the roller 48 is urged into engagement with a similar needle roller bearing 68 which extends through the slot 58.

It is apparent from FIG. 3 that load is applied to a beam specimen 70 mounted in the fixture through the hardened steel loading rollers 26, 36, 46 and 48 which are free to roll during loading so as to minimize axial friction loads. In addition, the rollers 46 and 48 which rest on the needle roller bearings 66 and 68, respectively, enable a single loading roller 46 and 48 to freely rotate relative to the plate 10 or 12 to which it is attached. As shown in FIG. 3, loading is applied to the fixture through a loading ball bearing 72 which engages the upper loading plate 10 in a recess 74 shown in FIG. 2.

While the preferred embodiment of the invention has been shown and described, it will be appreciated that various modifications may be made to the loading fixture without departing from the spirit of the invention or the scope of the subjoined claims. By way of example, it is contemplated that locating pins could be provided to facilitate alignment of the beam specimen center with the center of the loading spans X and Y and loading plates 10 and 12.

I claim:

1. A self-aligning, fully articulated four-point-bend loading fixture for modulus of rupture and fracture toughness testing of a brittle material specimen which is warped, twisted, or non-parallel comprising
   an inner fixed span provided by a first loading plate having a groove on each end thereof,
   a second loading plate spaced from said first loading plate for providing an outer span,
   pair of arms secured to opposite ends of said second loading plate facing the oppositely disposed grooves in said first loading plate,
   means on each of said arms for resiliently mounting a ball bearing for engaging said first loading plate in said grooves thereby centering said inner fixed span about said outer span while accommodating rotation of said upper loading plate with respect to said lower loading plate,
   a pair of first rollers mounted for rotation about spaced first axles carried by said first loading plate, the spacing between said first axles establishing said inner fixed span, and
   a pair of second rollers mounted for rotation about spaced second axles carried by said second loading plate, the spacing between said second axles establishing said outer span, said first and second pairs of rollers engaging said specimen for applying the load thereto.

2. A fully articulated four-point-bend loading fixture as claimed in claim 1 wherein the fixed span between the axles on the first loading plate is about 20 millimeters.

3. A fully articulated four-point-bend loading fixture as claimed in claim 1 wherein the fixed span between the axles on the second loading plate is about 40 millimeters.

4. A fully articulated four-point-bend loading fixture as claimed in claim 1 wherein each pair of first and second rollers comprises a hardened steel roller having a first diameter and another hardened steel roller having a diameter greater than said first diameter.

5. A fully articulated four-point-bend loading fixture as claimed in claim 4 wherein needle bearings are provided for engaging said other roller at right angles to its axis whereby said large diameter roller is free to rotate on an axis at a right angle to its axis of rotation.

6. In a self-aligning, fully articulated four-point-bend loading fixture of the type having a first pair of hardened steel rollers for engaging one surface of a brittle material specimen which is warped, twisted, or non-parallel to apply a load thereto at an inner fixed span and a second pair of hardened steel rollers for engaging an opposite surface of said specimen to apply a load thereto at an outer span for modulus of rupture and fractured toughness testing, the improvement comprising
   ball bearing means for accommodating rotation of said first pair of hardened steel rollers with respect to said second pair of hardened steel rollers,
   mounting means for positioning said first and second pairs of said hardened steel rollers at said spans on opposite sides of said specimen for free rotation as said load is applied,
   first needle bearings mounted at right angles to one of said first pair of rollers for engaging the same so that said one of said rollers is free to rotate on an axis at right angles to its axis of rotation, and
   second needle bearings mounted at right angles to one of said second pair of rollers for engaging the same so that said one of said second pair of rollers is free to rotate at right angles to its axis of rotation.

7. A fully articulated four-point-bend loading fixture as claimed in claim 6 wherein each pair of hardened steel rollers comprises one roller and another roller having a diameter greater than that of said one roller.

8. A fully articulated four-point-bend loading fixture as claimed in claim 7 wherein said needle bearings engage said other rollers at right angles to their axes whereby each large diameter roller is free to rotate on an axis at a right angle to its axis of rotation.

9. In a self-aligning, fully articulated four-point-bend-loading fixture of the type having a first pair of rollers for engaging one surface of a brittle material specimen which is warped, twisted, or non-parallel to apply a load thereto at an inner fixed span and a second pair of rollers for engaging an opposite surface of said specimen to apply a load thereto for modulus of rupture and fracture toughness testing, the improvement comprising spaced loading plates for mounting said first pair of rollers in spaced apart relationship establishing the inner fixed span and said second pair of rollers at a spacing establishing said outer span, said first and second pairs of rollers being mounted for rotation about their normal axes as said load is applied, a pair of arms secured to opposite ends of the loading plate that mounts said second pair of rollers facing oppositely disposed grooves in the loading plate that mounts said first pair of rollers, and a member carried by each of said arms for engaging one of said grooves thereby centering the inner fixed span about said outer fixed span while accommodating rotation of one of said loading plates with respect to the other loading plate.

10. A fully articulated four-point-bend loading fixture as claimed in claim 9 wherein the member carried by each arm comprises a ball bearing for engaging said one groove.

11. A fully articulated four-point-bend loading fixture as claimed in claim 10 including resilient means for urging said ball bearing into engagement with said groove.

* * * * *